United States Patent [19]

Hodge

[11] Patent Number: 4,539,713

[45] Date of Patent: Sep. 10, 1985

[54] CHIN OPERATED SHIELD AND WELDING HOOD

[75] Inventor: Raymond P. Hodge, Valparaiso, Ind.

[73] Assignee: Ram Corporation, East Chicago, Ind.

[21] Appl. No.: 574,915

[22] Filed: Jan. 30, 1984

[51] Int. Cl.³ .............................................. A61F 9/06
[52] U.S. Cl. ........................................................ 2/8
[58] Field of Search ........................... 2/8, 9, 427, 432

[56] References Cited

U.S. PATENT DOCUMENTS

| | | | |
|---|---|---|---|
| 2,719,972 | 10/1955 | Kelly | 2/8 |
| 3,086,213 | 4/1963 | Crozat et al. | 2/8 |
| 3,517,392 | 6/1970 | Hodge et al. | 2/8 |

Primary Examiner—Werner H. Schroeder
Assistant Examiner—J. L. Kravitz
Attorney, Agent, or Firm—Allegretti, Newitt, Witcoff & McAndrews, Ltd.

[57] ABSTRACT

An improved welding hood with a chin operated face shield provides hood stability, adjustability, ease of use, long life, an ability to hook the viewing window shield open, and positive closing of the shield otherwise. A linkage from the chin of the operator pivots the viewing window shield on the face shield. A spring biases the shield closed, is adapted to be hooked, and is attached to the shield and the linkage.

7 Claims, 5 Drawing Figures

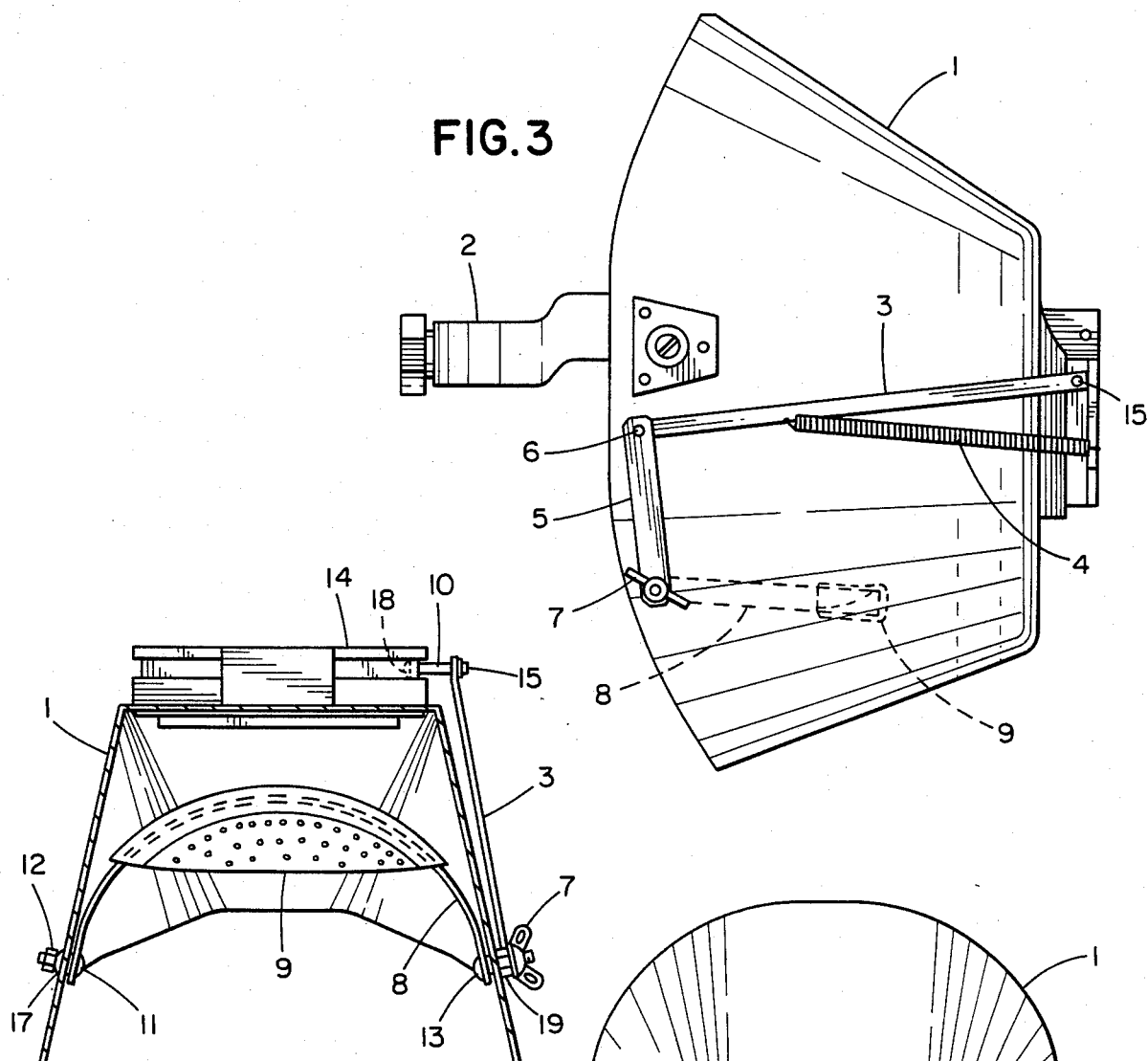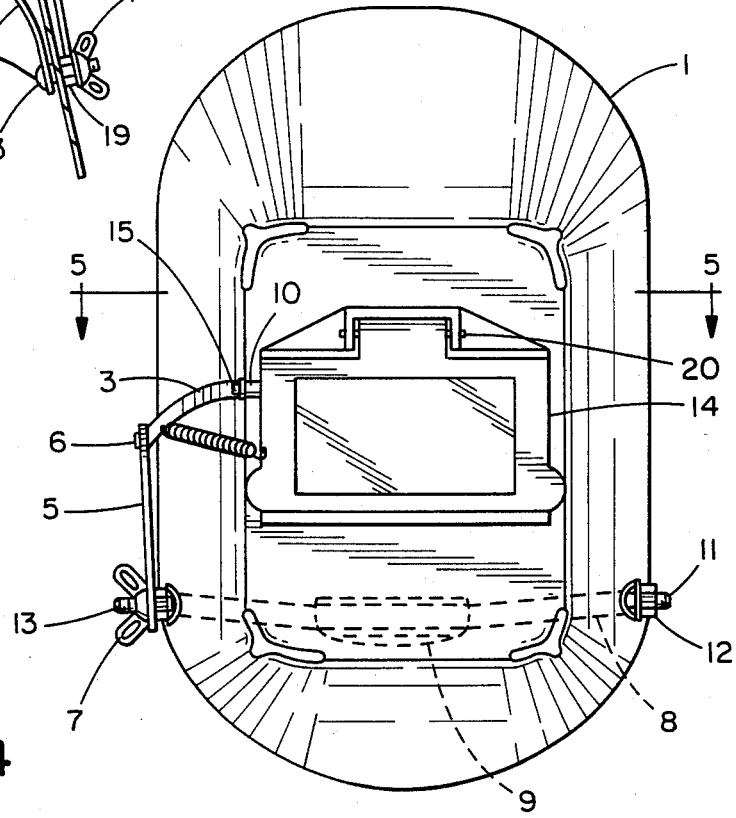

CHIN OPERATED SHIELD AND WELDING HOOD

BACKGROUND OF THE INVENTION

This invention relates to welding hoods, and more particularly, to welding hoods having openable window shields.

This invention is an improvement of the chin operated shield for a welding mask which is the subject of U.S. Pat. No. 3,517,392 issued on June 30, 1970, to William R. and Robert R. Hodge. The content of U.S. Pat. No. 3,517,392 is incorporated in this specification by reference.

SUMMARY OF THE INVENTION

In a principal aspect, this invention is an improved welding hood with a chin operated face shield. The hood comprises, first, the face shield having a viewing window, and a viewing window shield pivotably mounted on the face shield. Linkage means is pivotably mounted on the face shield, for pivotably moving the viewing window shield in response to chin movement. Biasing means is provided for biasing the viewing window shield closed over the viewing window. The biasing means is attached to the viewing window shield and the linkage means, in contrast to the hood of U.S. Pat. No. 3,517,392, where an over-center spring is attached to the shield and directly to the hood.

The invention as summarized above and hereinafter described in detail has at least seven substantial, beneficial advantages.

First, the invention provides stability of the welding hood during operation of the viewing window shield by chin movement of the user. Stability is highly desirable, and perhaps essential, to the use of the hood, because an unstable hood may disrupt the attention of the user to his torch, or obstruct his view.

Second, the viewing window shield is maintained in a fully closed position during all usage orientations of the hood, including downward-viewing orientations as required for welding with the user standing over the workpiece.

Third, the invention does not require a period of becoming accustomed to the operation of the viewing window shield. The invention provides a viewing window shield operation with a fine touch, which is quickly and readily operable.

Fourth, the invention provides a biasing means, e.g., a spring, which is only extended a small amount during operation. This minimal extension of the spring provides an extremely long spring life.

Fifth, the operating mechanism of the invention is readily adjustable to the physical features of differing users.

Sixth, the invention depends for driving force only upon downward movement of the chin. The invention does not depend upon upward driving movement of the chin, but only follows such upward movement. Operation of this type simplifies any chin pad included, provides more comfortable operation by the operator, and may reduce fatigue.

Seventh, the invention provides for long term opening of the viewing window shield from the viewing window, and return to chin operation, with the simple lifting of the spring to and from a position of being hooked on the linkage means.

These and other details, objects and advantages of the invention are further explained in a detailed description of the preferred embodiment of the invention, which follows a brief description of the drawing.

BRIEF DESCRIPTION OF THE DRAWING

The accompanying drawing includes five figures, as follows:

FIG. 3 is a side elevation view of the preferred embodiment, with the viewing window shield closed;

FIG. 4 is a front elevation view of the preferred embodiment as in FIG. 3; and

FIG. 5 is a cross-sectional view of the preferred embodiment from above the viewing window shield, as taken along line 5—5 of FIG. 4.

DETAILED DESCRIPTION OF THE PREFERRED EMBODIMENT

Figure 1:
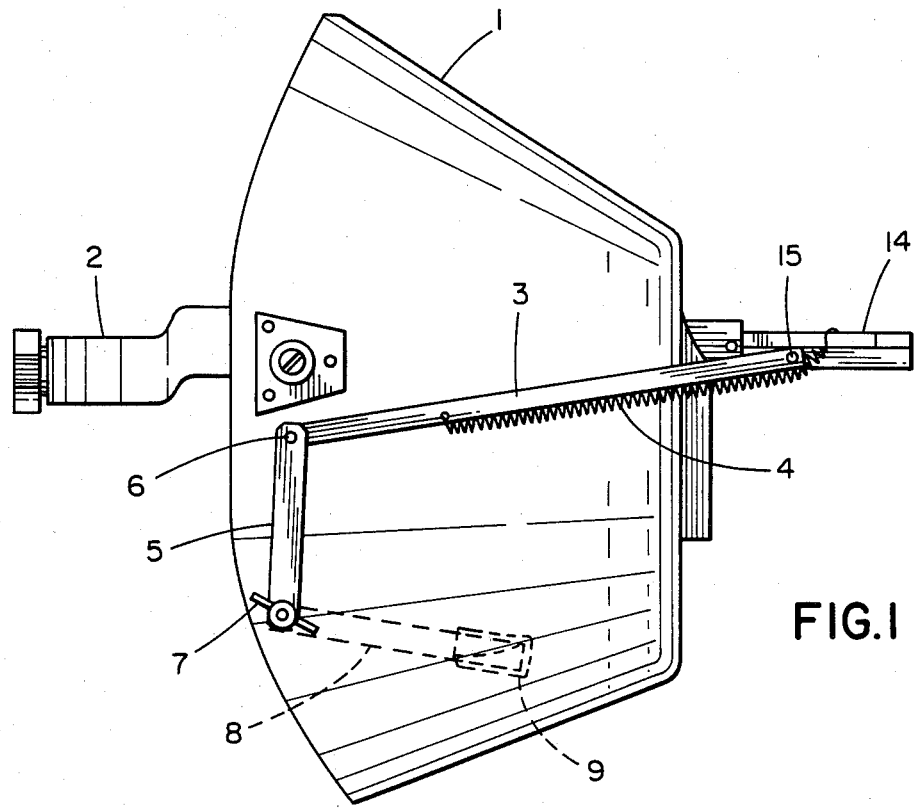
FIG. 1 is a side elevation view of the preferred embodiment of the present invention, with the viewing window shield open as would occur with the chin of the operator moved downward.
Figure 2:
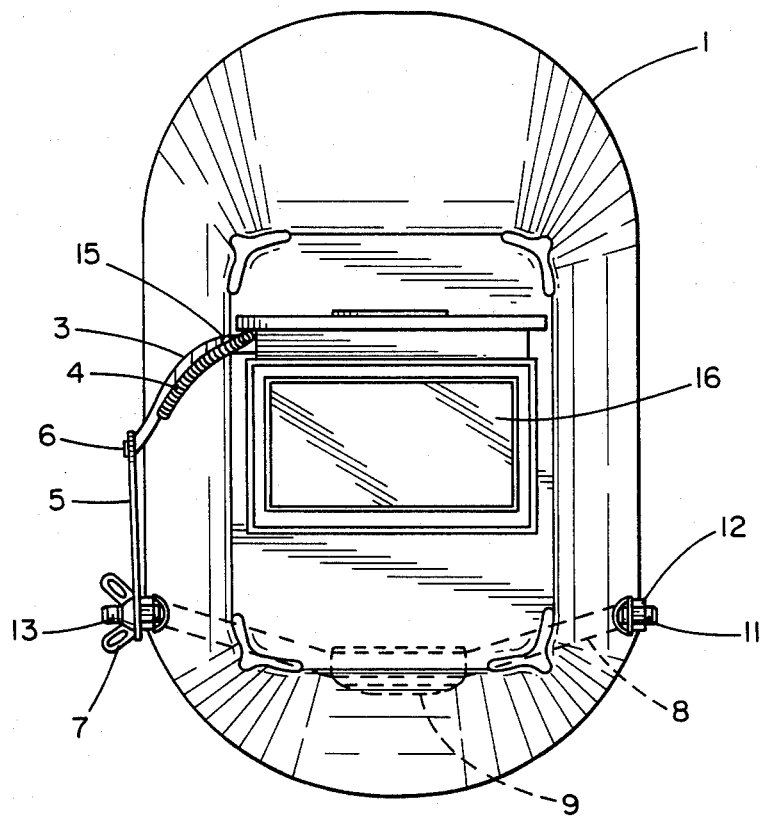
FIG. 2 is a front elevation view of the preferred embodiment, as in FIG. 1.

Referring to FIG. 1, the preferred embodiment of the present invention comprises a welding hood 1 shaped to cover and protect the face and sides, top and chin of the head of an operator. The hood 1 is placed on the head of the operator and is supported on the head by a head gear 2 pivotably attached to the hood 1.

The hood 1 as shown includes a viewing window provided by a viewing window frame and a grinding shield 16. As known to the art, the shield 16 may be absent in favor of an open window for operator sight. Alternatively, other glass or coverings may be provided in the window opening.

A viewing window shield, or lift shield, 14 is pinned to the viewing window frame, as best seen in FIG. 4. The shield 14 is pinned along the top of the viewing window frame, for pivoting movement about the horizontal pin 20 between the positions of the figures and all positions therebetween. The lift shield 14 is shaped to fully cover the window opening when closed against the window opening. The lift shield 14 may be opaque, or include a translucent welding viewing panel as shown.

As best seen in FIG. 5, a chin bar 8 supports a chin pad 9 and positions the pad for contact with and downward driving movement by the chin of the operator. The chin bar 8 extends from the chin pad 9 to the lower sides of the hood 1 adjacent the ears of the operator. At its ends, the chin bar 8 is pivotably mounted and fastened to the hood 1 by a pivot stud 13 and a pivot screw 11. A pivot screw nut is on the screw 11, and a pivot hex nut 19, and pivot wing nut 7 are on the stud 13. The pivot stud 13 and screw 11 extend through the ends of the chin bar 8 and through grommets in the sides of the welding hood 1. The chin bar 8 constitutes one form of an interior link for a linkage means, further exemplary links of which will be described.

Outside the welding hood 1, a first exterior or vertical lever 5 is mounted on the pivot stud 13. The vertical lever 5 is retained on the stud 13 by the pivot wing nut 7. The angle of the vertical lever 5 from the chin bar 8 is readily adjustable by loosening of the pivot wing nut 7, positioning of the vertical lever 5 and the chin bar 8, and retightening of the pivot wing nut 7. Adjustment is anticipated to occur between periods of welding, or when a new user dons the hood. During welding, and chin operated movement of the lift shield 14, the vertical lever 5 and the chin bar 8 are held in a fixed orientation to each other by the wing nut 7.

The vertical lever 5 extend substantially vertically upward from the pivot stud 13, and is linked at its upper ends to a second exterior link or horizontal lever 3 by a rivet 6. The horizontal lever 3 is pinned to pivot relative to the vertical lever 5, as shown by comparing FIGS. 1 and 3.

The horizontal lever 3 extends substantially horizontally and slightly upward from connection with the vertical lever 5 to a stud 18. The stud 18, having a cap 15, pivotably connects the horizontal lever 3 to the lift shield 14 at a distance from the pin 20 connecting the lift shield 14 to the hood 1.

As can be seen, downward movement of the chin rotates or pivots the chin bar 8 downward about the pivot screw 11 and the pivot stud 13, pivots the vertical lever 5 forward about the pivot stud 13, drives the horizontal lever 3 forward, and lifts the lift shield 14 in pivotal movement about the pin 20.

Return of the lift shield 14 to a closed position against the grinding shield 16, and maintenance of the lift shield 14 in the closed position, is provided by a spring 4, constituting one form of a spring biasing means or biasing means. The spring 4 is a helically wound, relatively light or low spring rate, and substantially long spring. The spring 4 is attached at one end to the horizontal lever 3 nearer the rivet 6 than the stud 18. The spring 4 is connected at its opposite end to the lift shield 14 substantially further from the pivoting pin 20 of the lift shield 14 than the stud 18. With the chin of the operator raised and his mouth closed, the lift shield 14 is in the closed position and the spring 4 has a tension sufficient to maintain the shield 14 closed against the grinding shield 16 in substantially all orientations of the hood 1. The spring 4 holds the shield 14 against the tendency caused by the weight of the shield 14 to open as the operator bends over and the hood moves to a downward-viewing orientation. As the operator moves his chin downward, the spring 4 is extended in a slight resistance to opening of the lift shield 14. In all positions of the lift shield 14, and unless manipulated by the operator, the spring 4 biases the shield 14 toward the closed position.

Should the operator desire to relieve his chin of the tension of the spring 4 and maintain the lift shield 14 open for an extended period of time, the invention and preferred embodiment provide that the spring 4 may be grasped adjacent the cap 15 and lifted over the cap 15. In this position, the spring 4 is hooked over the horizontal lever 3, and does not bias the lift shield 14 toward the closed position. Instead, the spring 4 is over center, and maintains the lift shield 14 in the fully open position. The operator may readily return the hood 1 to normal operation by grasping the spring 4 and returning the spring below the end of the horizontal lever 3.

The mechanism of the invention and preferred embodiment does not depend upon upward driving movement of the chin of the operator. Instead, the spring 4 provides that the links 3 and 5 drive the chin bar 8 upward as the chin is moved upward, following or tracking the movement of the chin.

As most preferred, the mechanism of the invention includes a spring 4 having one pound of initial tension, and a rate of 0.78 pounds per inch. Also as most preferred, the mechanism has dimensions relative to each other as scaled in the accompanying drawing.

The preferred embodiment of the invention, and the invention, are now described in such full, clear, concise and exact terms as to enable a person of ordinary skill in the art to make and use the same. As suggested above and otherwise, modifications may be made to the preferred embodiment without moving outside the scope of the invention. Therefore, to particularly point out and distinctly claim the subject matter regarded as invention, the following claims conclude this specification.

What is claimed:

1. An improved welding hood with a chain operated face shield comprising
    the face shield having a viewing window;
    a viewing window shield pivotably mounted on the face shield;
    linkage means pivotably mounted on the face shield for pivotably moving the viewing window shield in response to chin movement; and
    biasing means for biasing the viewing window shield closed over the viewing window, the biasing means having one end and an opposite end and being attached at the one end on the viewing window shield and at the opposite end to the linkage means.

2. A welding hood according to claim 1 in which the biasing means consists of a spring attached on the viewing window shield and to the linkage means.

3. A welding hood according to claim 1 in which the linkage means is further means for driving the viewing window shield open away from the viewing window in response to downward chin movement and the biasing means is further means for maintaining the viewing window shield closed over the viewing window during usage orientations of the hood including downward-viewing orientations.

4. A welding hood according to claim 1 in which the linkage means includes an interior link and a first exterior link pivotably attached together and to the hood, and a second exterior link pivotably attached to the first exterior link and the viewing window shield, and in which the biasing means is attached on the viewing window shield and to the second exterior link.

5. A welding hood according to claim 4 in which the biasing means consists of a single spring attached on the viewing window shield and to the second exterior link.

6. A welding hood according to claim 1 in which the biasing means is further means for providing for manually hooking of the biasing means on the linkage means, for providing manual, long-term opening of the viewing window shield from the viewing window.

7. A welding hood according to claim 1 in which the biasing means is further means for returning the viewing window shield closed over the viewing window by following upward chin movement and without upward, driving chin movement.

* * * * *